United States Patent [19]

Meul

[11] Patent Number: 4,983,743

[45] Date of Patent: Jan. 8, 1991

[54] 5-ALKYL TETRAMIC ACIDS

[75] Inventor: Thomas Meul, Visp, Switzerland

[73] Assignee: Lonza, Ltd., Gampel/Valais, Switzerland

[21] Appl. No.: 402,356

[22] Filed: Sep. 5, 1989

[30] Foreign Application Priority Data

Sep. 6, 1988 [CH] Switzerland .................. 3337/88

[51] Int. Cl.$^5$ ........................................ C07D 207/36
[52] U.S. Cl. ........................................... 548/544
[58] Field of Search ....................... 548/544; 544/544

[56] References Cited

U.S. PATENT DOCUMENTS

| | | | |
|---|---|---|---|
| 2,328,232 | 8/1943 | Schnider | 548/544 |
| 4,788,294 | 11/1988 | Duc et al. | 548/544 |
| 4,824,966 | 4/1989 | Meul et al. | 548/544 |
| 4,843,166 | 6/1989 | Meul | 548/544 |
| 4,855,451 | 8/1989 | Meul | 548/544 |

FOREIGN PATENT DOCUMENTS 0216324  9/1986  European Pat. Off. .
0252363  6/1987  European Pat. Off. .

OTHER PUBLICATIONS

Altenbach, H. J., Nachr. Chem. Tech. Lab., 36 (1988), pp. 756 to 758.
T. P. C. Mullholland et al., "Synthesis of Pyrolidine-2,4-Diones (Tetramic Acids) and Some Derivatives", Jnl. of Chem. Soc., Perkin Trans. I (1972), Organic and Bio-Organic Chemistry, pp. 2121-2128.
Patrick Jouin et al., "Stereospecific Synthesis of N-Protected Statine and its Analogues via Chiral Tetramic Acid", Jnl. Chem. Soc., Perkin Trans. I (1987) Organic and Bio-Organic Chemistry, pp. 1177-1182.
Jones et al., "A Synthesis of 3-Acyl-5-Alkyl Tetramic Acids", Tetrahedron Lett., (1978), pp. 3173-3176.
S. A. Harris et al., J. Med. Chem., 8, (1965), pp. 478-482.
G. Stork et al., "Carboxy-$\beta$-Lactams by Photochemical Ring Contraction", J. Am. Chem. Soc., 96, (1974) pp. 5787-5791.
C. O. Gitterman, "Antitumor, Cytotoxic, and Anibacterial Activities of Tetrazonic Acid and Congeneric Tetramic Acids", J. Med. Chem., 8, (1965), pp. 483-486.

*Primary Examiner*—David B. Springer
*Attorney, Agent, or Firm*—Fisher, Christen & Sabol

[57] ABSTRACT

A process for the production of 5-alkyl tetramic acids from 4-alkoxy-3-pyrrolin-2-ones and aldehyes or ketones. By basic catalysis, 5-alkylidene-4-alkoxy-3-pyrrolin-2-ones are first formed, which are converted into the target compounds by cleavage of the alkoxy group and catalytic hydrogenation.

12 Claims, No Drawings

5-ALKYL TETRAMIC ACIDS

BACKGROUND OF THE INVENTION

1. Field Of The Invention

The invention relates to a multistep process for the production of 5-alkyl tetramic acids from 4-alkyloxy- or 4-benzyloxy-3-pyrrolin-2-ones and aldehydes or ketones. It further relates to new 5-alkyl tetramic acids, which are accessible this way.

2. Background Art

5-Alkyl tetramic acids are valuable intermediate products for the production of beta-hydroxy-gamma-amino acids, such as, statine, which, for its part, plays an essential role as a structural element of renin inhibitors, such as, pepstatin or its analogs modified in the side chain. Renin inhibitors exhibit promising physiological effects and, therefore, are suitable for therapeutic purposes, especially as antihypertensive agents [H. J. Altenbach, Nachr. Chem. Tech. Lab. 36, 756 (1988)]. The tetramic acids can be present, depending on the conditions and the substituents, in the dione form, i.e., as pyrrolidine-2,4-dione, or in the enolone form, i.e., as 4-hydroxy-3-pyrrolin-2-one, or as mixture of the two forms. Only the dione form is represented below in each case regardless of the actual conditions.

So far there has been lacking simple and cost-favorable processes for the production of variously substituted 5-alkyl tetramic acids.

Thus, from Jouin et al., J. Chem. Soc. Perkin Trans. I, 1987, 1177, it is known to condense N-protected alpha-amino acids, after activation with chloroformic acid isopropenyl ester in the presence of 4-dimethylaminopyridine with Meldrum's acid, to the corresponding (1-hydroxyalkylidene) Meldrum's acids, which on heating in solution eliminate acetone and $CO_2$ and are converted into the N-protected 5-substituted tetramic acids. Such process does yield optically active tetramic acid derivatives, if a start is made from optically active natural alpha-amino acids, but a whole series of expensive starting materials that are partially difficult to obtain or highly toxic, which in practice rules out a technical application.

Another drawback of such process is the limitation of the possibilities of variation of the substituents in the end product, which results from the fact that with the alpha-amino acids only a limited choice of substituents is available.

The same drawbacks are exhibited by an older process, which starts from alpha-amino acid esters, which are first reacted with malonic acid ester chlorides to the corresponding N-(alkoxycarbonylacetyl)-alpha-amino acid esters. The latter are cyclized to the 3-alkoxycarbonyl tetramic acids, which are converted into the corresponding 5-substituted tetramic acids by hydrolysis and decarboxylation. (T. P. C. Mulholland, R. Foster and D. B. Haydock, J. Chem. Soc. Perkin Trans. I 1972, 2121).

BROAD DESCRIPTION OF THE INVENTION

The main object of the invention is to provide a process which does not exhibit the above-mentioned drawbacks and makes available a broad spectrum of differently substituted tetramic acids. Other objects and advantages of the invention are set out herein or are obvious herefrom to one skilled in the art.

The objects and advantages of the invention are achieved by the processes and compounds of the invention.

Applicant's invention involves a process for the production of substituted tetramic acids of formula:

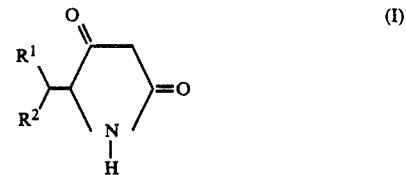

or their tautomers, wherein:

(a) $R^1$ is a straight-chain or branched alkyl group having 1 to 6 C atoms or a cycloalkyl group having 4 to 7 C atoms or a group of the form $—[CH_2]_n—Q$ with n being 1 or 2 and Q being one of the above-mentioned cycloalkyl groups or a phenyl group, and $R^2$, independently therefrom, is hydrogen or a straight-chain alkyl group having 1 to 4 C atoms; or (b) $R^1$ and $R^2$ together are an optionally branched alkanediyl group, which, in connection with the linking C atom, forms a 4- to 7-member ring optionally substituted with one or more lower alkyl groups.

In a first step, a 3-pyrrolin-2-one of the formula:

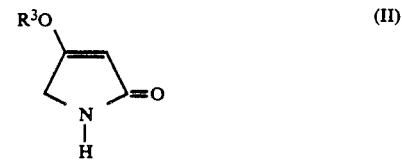

wherein $R^3$ is a straight-chain or branched alkyl group having 1 to 4 C atoms or a benzyl group optionally substituted with one or more lower alkyl groups, is reacted with an aldehyde or ketone of the formula:

or

wherein $R^1$ is a straight-chain or branched alkyl group having 1 to 6 C atoms or a cycloalkyl group having 4 to 7 C atoms or a group of the form $—[CH_2]_n—Q$ with n being 1 or 2 and Q being one of the above-mentioned cycloalkyl groups or a phenyl group, and $R^2$, independently therefrom, is hydrogen or a straight-chain alkyl group having 1 to 4 C atoms and $R^4$ is a group, which differs from $R^1$ only by the presence of one or more double or triple bonds not belonging to any aromatic system and not conjugated with the carbonyl group. The reaction takes place in solution in the presence of a base and first leads to a 5-alkylidene-3-pyrrolin-2-one of the formula:

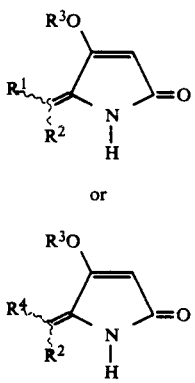

(IVa)

or (IVb)

wherein $R^1$, $R^2$, and $R^4$ have the above-mentioned meanings.

The 4-alkoxy or 4-benzyloxy-3-pyrrolin-2-one of formula (II) can be obtained according to known processes. 4-Alkoxy-3-pyrrolin-2-one can be produced according to European Published Patent Application No. 021632 from 4-haloacetic acid esters with orthoformic acid esters and ammonia. 4-Benzyloxy-3-pyrrolin-2-one can be produced according to European Published Patent Application No. 0252363 from 4-methoxy-3-pyrrolin-2-one and the corresponding benzyl alcohols. As the radical $R^3$, the 3-pyrrolin-2-ones suitably contain an alkyl group with up to 4 C atoms, for example, methyl, ethyl, propyl, isopropyl or butyl, or a benzyl group, which optionally can be substituted with one or more alkyl groups having up to 4 C atoms, such as, o-methylbenzyl, m-methylbenzyl, p-methylbenzyl, 2,4-dimethylbenzyl, 3,5-dimethylbenzyl, p-ethylbenzyl, p-isopropylbenzyl, p-butylbenzyl or p-tert-butylbenzyl. Preferred radicals $R^3$ are methyl, ethyl, propyl, isopropyl or benzyl; methyl is especially preferred.

Useful aldehydes or ketones of general formula (IIIa) or (IIIb) include saturated aliphatic aldehydes having 2 to 7 C atoms, namely, straight-chain such as acetaldehyde, propionaldehyde, butyraldehyde, valeraldehyde, caproaldehyde or enanthaldehyde, or branched, such as, isobutyraldehyde, isovaleraldehyde, pivalaldehyde, isocaproaldehyde, 2-methylvaleraldehyde or 2-ethylbutyraldehyde, or saturated alicyclic aldehydes having 5 to 8 C atoms, such as, cyclobutanecarbaldehyde, cyclopentanecarbaldehyde, cyclohexanecarbaldehyde or cycloheptanecarbaldehyde, or cycloalkylacetaldehydes, such as, cyclohexylacetaldehyde, cycloalkylpropionaldehydes, such as, 3-cyclohexylpropionaldehyde, arylacetaldehydes, such as phenylacetaldehyde, arylpropionaldehydes, such as, 3-phenylpropionaldehyde, or aliphatic ketones, such as, acetone, ethyl methyl ketone, isopropyl methyl ketone, diethyl ketone, isobutyl methyl ketone, 2-heptanone, 3-heptanone, 4-heptanone, 2-octanone or 5-nonanone, or alicyclic ketones, such as, cyclobutanone, cyclopentanone, cyclohexanone or cycloheptanone. It is within the scope of the invention to use unsaturated aldehydes or ketones instead of the corresponding saturated ones, for example, 3-cyclohexenecarbaldehyde instead of cyclohexanecarbaldehyde. A requirement in this case is that the multiple bonds not be in conjugation with the carbonyl group, since otherwise other reaction paths come to the fore. In these cases, the double or triple bonds in the last process step, i.e., the catalytic hydrogenation, are also hydrogenated.

If aldehydes or unsymmetrical ketones are used, two geometric isomers, namely, the Z and E forms of the corresponding 5-alkylidene-3-pyrrolin-2-one, are formed. Which of the two forms is formed or whether both side by side are produced, depends on the radicals $R^1$ or $R^4$ and $R^2$. For the further course of the reaction it is not essential whether the Z or E form or a mixture results.

The reaction of the 3-pyrrolin-2-one with the aldehyde or ketone is performed with a base as catalyst in solution. Preferably an alkali hydroxide, especially preferably sodium hydroxide, is used as base.

Polar protic solvents, such as, water or lower alcohols, are suitable as solvents, preferably water alone or in mixture with a lower alcohol is used. The reaction is suitably performed at a temperature of 20° to 100° C., preferably at 30° to 50° C. The reaction period is suitably 5 minutes to 5 hours. The molar ratio of 3-pyrrolin-2-one (II) to aldehyde or ketone (III) is suitably 1:1 to 1:5, preferably 1:1 to 1:1.5.

In the following step the 5-alkylidene-3-pyrrolin-2-one of formula (III), by cleavage of radical $R^3$ under acid catalysis, is converted into a 5-alkylidene tetramic acid of formula:

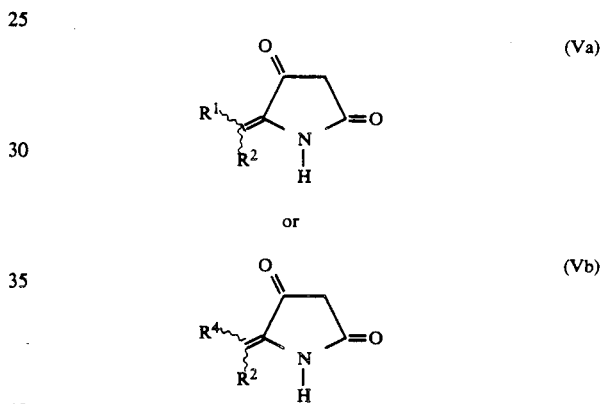

(Va)

or (Vb)

This step can be skipped if $R^3$ is a benzyl group or a substituted benzyl group, since benzyl groups are also cleavable under conditions of catalytic hydrogenation (see European Published Patent Application No. 0252363). This is particularly advantageous if such compounds according to the invention are to be produced which, under conditions of acid-catalyzed cleavage, tend to side reactions. The acid-catalyzed cleavage can be performed with strong acids in polar protic solvents, such as, water or aqueous solvent mixtures or lower carboxylic acids. In a preferred embodiment, hydrogen chloride or hydrogen bromide in acetic acid is used, hydrogen chloride is especially preferred. Another preferred embodiment uses sulfuric acid in aqueous tetrahydrofuran or dioxane. The reaction temperature is suitably 20° to 100° C., preferably 20° to 60° C.

In the last process step, the exocyclic double bond as well as optionally other double or triple bonds present in the radical $R^4$ are hydrogenated on a palladium catalyst. At the same time, if radical $R^3$ is a benzyl group or substituted benzyl group and was not cleaved by acid, $R^3$ is removed by hydrogenolysis. Thus, a chirality center is formed in position 5 of the pyrroline or pyrrolidine ring and, if $R^2$ is different from $R^1$ and is not hydrogen, in the alpha-position of the side chain, so that the resulting tetramic acid is obtained as an enantiomeric or diastereomeric mixture.

The catalyst can be applied to a support material, such as, activated carbon or aluminum oxide. The hydrogenation is suitably performed in a solvent, such as, methanol or ethyl acetate; for this purpose, all solvents usual for catalytic hydrogenation can be used. The hydrogen pressure in the hydrogenation is not critical; preferably it is 1 to 50 bars. Preferably hydrogenation is performed at a temperature of 10° to 60° C.; it is especially preferred at room temperature.

DETAILED DESCRIPTION OF THE INVENTION

The following examples illustrate embodiments of the process according to the invention. In the examples, all $^1$H NMR spectra were taken in CDCl$_3$ at 300 MHz.

EXAMPLE 1

(Z)-4-methoxy-5-isobutylidene-3-pyrrolin-2-one (IV, $R^2$=H, $R^3$=Me, $R^4$=isopropyl)

35.9 g of 4-methoxy-3-pyrrolin-2-one (II, $R^3$=Me) was dissolved in 2000 ml of 4 n aqueous sodium hydroxide solution and was mixed at 50° C. within 30 minutes with a solution of 24.0 g of isobutyraldehyde in 675 ml of methanol. After 1 hour, 675 ml of water was added and the reaction mixture was cooled to 0° C. The resulting product was filtered off, washed with water and dried in a vacuum at 40° C. The filtrate was extracted with dichloromethane. The yield was 39.7 g plus 10.1 g from the dichloromethane extract (99.4 percent total yield). Other data for the product was:

Melting point: 139° to 141° C., colorless crystals $^1$H-NMR: δ=8.64 (br.s, 1H), 5.30 (d, 1H), 5.14 (d, 1H), 3.85 (s, 3H), 2.67 (m, 1H), 1.11 (d, 6H)

EXAMPLE 2

(Z)-4-methoxy-5-(cyclohexylmethylene)-3-pyrrolin-2-one (IV, $R^2$=H, $R^3$=Me, $R^4$=cyclohexyl)

23.9 g of 4-methoxy-3-pyrrolin-2-one (94.6 percent) in 1360 ml of 4 n sodium hydroxide solution and 27.5 g of cyclohexanecarbaldehyde (90 to 95 percent) in 330 ml of methanol were reacted as described in Example 1. Data for the product was:

Yield: 39.8 g (96.1 percent) Melting point: 134° to 136° C., colorless crystals $^1$H-NMR: δ=9.07 (br.s, 1H), 5.32 (d, 1H), 5.14 (d, 1H), 3.83 (s, 3H), 2.40 (m, 1H), 1.09–1.81 (m, 10H)

EXAMPLE 3

(Z)-4-methoxy-5-propylidene-3-pyrrolin-2-one (IV, $R^2$=H, $R^3$=Me, $R^4$=Et)

23.9 g of 4-methoxy-3-pyrrolin-2-one (94.6 percent) in 1360 ml of 4 n sodium hydroxide solution and 13.2 g of propionaldehyde (97 percent) in 330 ml of methanol were reacted as described in Example 1. Data for the product was:

Yield: 18.0 g (58.8 percent) Melting point: 119° to 127° C., colorless crystals $^1$H-NMR: δ=8.62 (br.s, 1H) 5.43 (t, 1H), 5.12 (d,1H), 3.84 (s, 3H), 2.27 (m, 2H), 1.12 (t, 3H)

EXAMPLE 4

(Z)-4-methoxy-5-(2-ethybutylidene)-3-pyrrolin-2-one (IV, $R^2$=H, $R^3$=Me, $R^4$=3-pentyl)

The synthesis took place as described in Example 1 but with 2-ethylbutyraldehyde as the carbonyl compound. Data for the product was:

Yield: 73.5 percent Melting point: 128° to 130° C., colorless crystals $^1$H-NMR: δ=8.38 (br.s, 1H), 5.20 (d, 1H), 5.13 (d, 1H), 3.85 (s, 3H), 2.17 (m, 4H), 1.25–1.65 (M, 4H), 0.89 (t, 6H)

EXAMPLE 5

(±)-(Z)-4-methoxy-5-(2-methylpentylidene)-3-pyrrolin-2-one (IV, $R^2$=H, $R^3$=Me, $R^4$=2-pentyl)

The synthesis took place as described in Example 1 but with 2-methylyaleraldehyde as the carbonyl compound. Data for the product was:

Yield: 73.3 percent Melting point: 83° to 87°, colorless crystals $^1$H-NMR: δ=8.05 (br.s, 1H), 5.25 (d, 1H), 5.12 (d, 1H), 3.85 (s, 3H), 2.45 (m, 1H), 1.20–1.50 (m, 4H), 1.09 (d, 3H), 0.90 (t, 3H)

EXAMPLE 6

(Z)-4-methoxy-5-isooentylidene-3-pyrrolin-2-one (IV, $R^2$=H, $R^3$=Me, $R^4$=isobutyl)

The synthesis took place as described in Example 1 but with isovaleraldehyde as carbonyl compound. Data for the product was:

Yield: 92.8 percent Melting point: 90° to 92° C., colorless crystals $^1$H-NMR: δ=8.60 (br.s, 1H), 5.46 (t, 1H), 5.13 (d, 1H), 3.84 (s, 3H), 2.14 (dd, 2H), 1.79 (m, 1H), 0.97 (d, 6H)

EXAMPLE 7

(Z)-4-methoxy-5-(2,2-dimethylpropylidene)-3-pyrrolin-2-one (IV, $R^2$=H, $R^3$=Me, $R^4$=tert-butyl)

The synthesis took place as described in Example 1 but with pivalaldehyde as carbonyl compound. Data for the product was:

Yield: 54.5 percent Melting point: 165° to 167° colorless crystals 1H-NMR: δ6.92 (br.s, 1H), 5.37 (s, 1H), 5.08 (d, 1H), 3.84 (s, 3H), 1.22 (s, 9H)

EXAMPLE 8

4-Methoxy-5-isopropylidene-3-pyrrolin-2-one (IV, $R^2$=$R^3$=$R^4$=Me)

The synthesis took place as described in Example 1 but with three equivalents of acetone as the carbonyl compound and without addition of methanol. Data for the product was:

Yield: 75.8 percent Melting point: 246° to 248° C., colorless crystals $^1$H-NMR: δ=8.27 (br.s, 1H), 5.19 (d, 1H), 3.84 (s, 3H), 2.11 (s, 3H), 1.93 (s, 3H)

EXAMPLE 9

4-Methoxy-5-(1-methylpropylidene)-3-pyrrolin-2-one (E/Z mixture)

(IV, R$^2$=R$^3$=Me, R$^4$=Et)

The synthesis took place as described in Example 8 but with 2-butanone as carbonyl compound. Data for the product was:

Yield: 34.7 percent Melting point: 119° to 122° C., colorless crystals $^1$H-NMR: δ=7.29 (br.s, 1H), 5.18 (d, 1H), 3.82 (s, 3H), 2.52 (q, 1H), 2.25 (q, 1H), 2.08 (s, 3H), 1.95 (s, 3H), 111 (t, 3H), 1.07 (t, 3H)

EXAMPLE 10

(±)-(Z)-4-methoxy-5-(3-cyclohexen-1-yl-methylene)-3-pyrrolin-2-one (IV, R$^2$=H, R$^3$=Me, R$^4$=3-cyclohexen-1-yl)

The synthesis took place as described in Example 1 but with 3-cyclohexen-1-aldehyde (1,2,3,6-tetrahydrobenzaldehyde) as carbonyl compound. Data for the product was:

Yield: 97.1 percent Melting point: 152° to 162° C., colorless crystals $^1$H-NMR: δ=7.87 (br.s, 1H), 5.62–5.79 (m, 2H), 5.40 (d, 1H), 5.13 (d, 1H), 3.84 (s, 3H), 2.58 (m, 1H), 1.44–2.29 (m, 6H)

EXAMPLE 11

(Z)-4-benzyloxy-5-isobutylidene-3-pyrrolin-2-one (IV, R$^2$=H, R$^3$=benzyl, R$^4$=isopropyl)

This synthesis took place as described in Example 1 but with 4-benzyloxy-3-pyrrolin-2-one (II, R$^3$=benzyl) instead of 4-methoxy-3-pyrrolin-2-one. Data for the product was:

Yield: 57.6 percent Melting point: 159° to 161° C., colorless crystals $^1$H-NMR: δ=8.17 (br.s, 1H), 7.30–7.45 (m, 5H), 5.38 (d, 1H), 5.20 (d, 1H), 5.03 (s, 2H), 2.62 (m, 1H), 1.11 (d, 6H)

EXAMPLE 12

(Z)-5-isobutylidenepyrrolidine-2,4-dione ((Z)-isobutylidene tetramic acid)

(Va, R$^1$=isopropyl, R$^2$=H)

39.7 g of (Z)-4-methoxy-5-isobutylidene-3-pyrrolin-2-one (produced according to Example 1) was dissolved in 390 ml of acetic acid. The solution was saturated with hydrogen chloride gas at 40° to 45° C. within 10 hours and then concentrated by evaporation in a vacuum. Data for the product was:

Yield: 49.3 g Melting point: 140° to 142° (from water), yellowish crystals $^1$H-NMR: δ=9.68 (br.s, 1H), 5.58 (d, 1H), 3.12 (s, 2H), 2.55 (m, 1H), 1.12 (d, 6H)

TABLE 1

| Example | Name | Structure | Feedstock From Example | Melting Point [°C.] | $^1$H-NMR-Spectrum |
|---|---|---|---|---|---|
| 13 | (Z)-5-(Cyclohexyl-methylene)-pyrrolidin-2,4-dione | Va, R$^1$ = Cyclohexyl, R$^2$ = H | 2 | 168°–170° | 9.37 (br.s, 1H), 5.61 (d, 1H), 3.12 (s, 2H), 2.22 (m, 1H), 1.13–1.82 (m, 10H) |
| 14 | (Z)-5-Propylidene pyrrolidin-2,4-dione | Va, R$^1$ = Et, R$^2$ = H | 3 | 134°–136° | 10.07 (br.s, 1H), 5.72 (t, 1H), 3.13 (s, 2H), 2.20 (m, 2H), 1.13 (t, 3H) |
| 15 | (Z)-5-(2-Ethylbutylidene)-pyrrolidin-2,4-dione | Va, R$^1$ = 3-Pentyl, R$^2$ = H | 4 | 127°–129° | 9.78 (br.s, 1H), 5.51 (d, 1H), 3.13 (s, 2H), 2.12 (m, 1H), 1.25–168 (m, 4H) 0.89 (t, 6H) |
| 16 | (±)-(Z)-(1-Methyl pentylidene-pyrrolidin-2,4-dione | Va, R$^1$ = 2-Pentyl, R$^2$ = H | 5 | 115°–117° | 9.40 (br.s, 1H), 5.53 (d, 1H), 3.12 (s, 2H), 2.38 (m, 1H), 1.25–1.53 (m, 4H) 1.09 (d, 3H), 0.91 (t, 3H) |
| 17 | (Z)-5-Isopentylidene-pyrrolidin-2,4-dione | Va, R$^1$ = Isobutyl, R$^2$ = H | 6 | 114°–115° | 9.97 (br.s, 1H), 5.76 (t, 1H), 3.12 (s, 2H), 2.09 (dd, 1H), 1.82 (m, 1H), 0.97 (d, 6H) |
| 18 | (Z)-5-(2,2-Dimethyl-propylidene)-pyrrolidin-2,4-dione | Va, R$^1$ = tert-Butyl, R$^2$ = H | 7 | 106°–108° | 8.42 (br.s, 1H), 5.67 (s, 1H), 3.04 (s, 2H), 1.22 (s, 9H) |
| 19 | 5-Isopropylidene-pyrrolidin-2,4-dione | Va, R$^1$ = R$^2$ = Me | 8 | 187°–188° | 9.43 (br.s, 1H), 3.11 (s, 2H), 2.20 (s, 2H), 1.89 (s, 3H) |
| 20 | (±)-(Z)-5-(3-Cyclohexene-1-yl-methylene)-pyrrolidin-2,4-dione | Vb, R$^2$ = H, R$^4$ = 3-Cyclohexen-1-yl | 10 | | 5.60–5.80 (m, 3H), 3.13 (s, 2H), 2.55 (m, 1H), 1.45–2.30 (m, 6H) |

EXAMPLES 13 and 20

The compounds listed in Table 1 were produced analogously to Example 12. The yields are almost quantitative (more than 95 percent): all of the compounds are yellow.

EXAMPLE 21

(±)-5-isobutyl-pyrrolidine-2,4-dione [(±)-5-isobutyl tetramic acid]

(1, R$^1$=isopropyl, R$^2$=H)

10.0 g of (Z)-5-isobutylidene-pyrrolidine-2,4-dione (raw product from Example 12) was dissolved in 200 ml of ethyl acetate and mixed with 1.0 g of palladium/activated carbon (5 percent Pd). It was hydrogenated at room temperature and 20 bars of hydrogen pressure in an autoclave with stirring for four hours, then the catalyst was filtered off and the solvent was distilled of. The yield was 7.4 g of raw product (98 percent relative to the 5-isobutylidene-4-methoxy-3-pyrrolin-2-one). Other data for product was:

Melting point: 113° to 117° C. (from ethyl acetate/hexane) yellowish crystals $^1$H-NMR: δ=8.05 (br.s, 1H), 4.04 (dd, 1H), 3.04 (s, 2H), 1.44–1.89 (m, 3H), 0.97 (dd, 6H)

EXAMPLES 22 to 26

The compounds listed in Table 2 were produced analogously to Example 21. The yields relate in each case to the corresponding compound V; all compounds are colorless.

TABLE 2

| Example | Name | Structure | Feedstock From Example | Melting Point [°C.] | Yield [%] | $^1$H-NMR-Spectrum |
|---|---|---|---|---|---|---|
| 22 | (±)-5-(Cyclohexylmethyl)-pyrrolidin-2,4-dinone | I, $R^1$ = Cyclohexyl, $R^2$ = H | 13 | 169°–171° | 83.2 | 7.00 (br.s, 1H), 4.07 (dd, 1H), 3.04 (s, 2H), 0.85–1.80 (m, 13H) |
| 23 | (±)-5-(2-Ethylbutyl)-pyrrolidin-2,4-dione | I, $R^1$ = 3-Pentyl, $R^2$ = H | 15 | 78°–80° | 71.7 | 7.30 (br.s, 1H), 4.04 (dd, 1H).3.03 (s, 2H), 1.22–1.84 (m, 7H), 0.82–0.97 (m, 6H) |
| 24 | (±)-5-Propyl-pyrrolidin-2,4-dione | I, $R^1$ = Et, $R^2$ = H | 14 | 101°–103° | 97.6 | 7.20 (br.s, 1H), 4.03 (dd, 1H), 3.03 (s, 2H), 1.32–1.90 (m, 4H), 0.98 (t, 3H) |
| 25 | (±)-5-Isopentyl-pyrrolidin-2,4-dione | I, $R^1$ = Isobutyl, $R^2$ = H | 17 | 124°–126° | 88 | 7.09 (br.s, 1H), 4.01 (dd, 1H), 3.02 (s, 2H), 1.12–1.91 (m, 5H), 0.92 (dd, 6H) |
| 26 | (±)-5-(2-Methylpentyl)-pyrrolidin-2,4-dione (Diastereomeric mixture) | I, $R^1$ = 2-Pentyl, $R^2$ = H | 16 | 98°–101° | 73 | 7.10 (br.s, 1H)* 6.98 (br.s, 1H)** 4.00–4.10 (m, 1H)*** 3.03 (s, 2H)* * * 0.85–1.90 (m, 13H)*** |

*Diastereomer A
**Diastereomer B
***Diastereomers A + B

EXAMPLE 27

(±)-5-Isobutyl-pyrrolidine-2,4-dione (I, $R^1$=isopropyl, $R^2$=H)

4.0 g of (Z)-4-benzyloxy-5-isobutylidene-3-pyrrolin-2-one (produced according to Example 11) was dissolved in 50 ml of ethyl acetate and mixed with 0.4 g of palladium/activated carbon (5 percent Pd). It was hydrogenated at room temperature and 20 bars of hydrogen pressure in an autoclave with stirring for 7 hours, then the catalyst was filtered off and the solvent was distilled off. The yield was 2.6 g of colorless crystals The physical data was identical with the product according to Example 21.

What is claimed is:

1. Substituted tetramic acid of the formula:

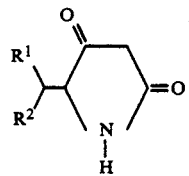

or a tautomer thereof, wherein
(a) $R^1$ is a straight-chain or branched alkyl group having 2 to 6 atoms or a cycloalkyl group having 4 to 7 C atoms or a group of the form —[CH$_2$]$_n$—Q with n being 1 or 2, and Q being one of the above-mentioned cycloalkyl groups or a phenyl group, and $R^2$, independently therefrom, is hydrogen or a straight-chain alkyl group having 1 to 4 C atoms, or
(b) $R^1$ or $R^2$ together are an optionally branched alkanediyl group, which, in connection with the linking C atom, forms a 4- to 7-member ring optionally substituted with one or more lower alkyl groups, except 5-benzyl tetramic acid, 5-(2-butyl) tetramic acid, 5-isobutyl tetramic acid and 5-n-hexyl tetramic acid.

2. Compound according to claim 1 wherein $R^2$ is hydrogen.

3. 5-(Cyclohexylmethyl) tetramic acid.

4. 5-(2-ethylbutyl) tetramic acid.

5. 5-propyl tetramic acid.

6. 5-isopentyl tetramic acid.

7. 5-(2-methylpentyl) tetramic acid.

8. Compound according to claim 1 wherein $R^1$ is a straight-chain or branched alkyl group having 2 to 6 carbon atoms.

9. Compound according to claim 1 wherein $R^1$ is a cycloalkyl group having 4 to 7 carbon atoms.

10. Compound according to claim 1 wherein $R^1$ is a group of the form —[CH$_2$]$_n$—Q where n is 1 or 2, and Q is a cycloalkyl group having 4 to 7 carbon atoms or a phenyl group.

11. Compound according to claim 1 wherein $R^2$ is a straight-chain alkyl group having 1 to 4 carbon atoms.

12. Compound according to claim 1 wherein $R^1$ or $R^2$ together in an optionally branched alkanediyl group, which, in connection with the linking carbon atom, forms 4 to 7 carbon member ring.

* * * * *